United States Patent [19]

Hsu

[11] Patent Number: 4,928,697

[45] Date of Patent: May 29, 1990

[54] NON-CONTACT HIGH FREQUENCY TONOMETER

[75] Inventor: Hsiung Hsu, Columbus, Ohio

[73] Assignee: The Ohio State University, Columbus, Ohio

[21] Appl. No.: 250,165

[22] Filed: Sep. 28, 1988

[51] Int. Cl.[5] .............................................. A61B 3/16
[52] U.S. Cl. ................................. 128/649; 128/660.02
[58] Field of Search ............... 128/645, 646, 647, 649, 128/653, 660.02, 660.06, 661.02, 748, 774, 782; 73/524, 589, 605, 627

[56] References Cited

U.S. PATENT DOCUMENTS

| | | | |
|---|---|---|---|
| 3,763,696 | 10/1973 | Krakau | 128/645 |
| 3,948,248 | 4/1976 | Zuckerman et al. | 128/676 |
| 4,610,255 | 9/1986 | Shimura et al. | 128/660.7 |
| 4,819,649 | 4/1989 | Rogers et al. | 128/660.2 |

Primary Examiner—William E. Kamm
Attorney, Agent, or Firm—Emch, Schaffer, Schaub & Porcello Co.

[57] ABSTRACT

A non-contact tonometer for use in the measurement of intraocular pressure in the diagnosis of glaucoma utilizes low frequency sound to perturb a given corneal area. High frequency sound waves are directed toward the perturbed corneal area and reflected therefrom. The output signals created by amplitude modulation of the the reflected sound waves are directly related to the intraocular pressure. The tonometer eliminates the need for physical contact with the eye, topical anesthetization and has no audible sound with no visible light or other sensory impacts on the eye.

4 Claims, 4 Drawing Sheets

NON-CONTACT HIGH FREQUENCY TONOMETER

BACKGROUND OF THE INVENTION

This present invention is directed toward an improved tonometer system for use in the early detection of glaucoma. Specifically, the tonometer of the present invention provides for a accurate measurement of the intraocular pressure without making any physical contact with the eye and without need for eye drops or anesthetization. The tonometer of the present invention achieves these measurements without the use of detached sound, detached light, or a surge of air to the eye.

Glaucoma is an eye disease which is one of the leading causes of blindness in the U.S. and throughout the world. Glaucoma is fairly common in adults over age 35. Two out of every 100 persons in this age group have vision threatened by glaucoma.

When an object is viewed, the image is carried from the retina of the eye to the brain by the optic nerve. The optic nerve is an accumulation of over a million individual transmitters, each carrying a message to the brain. The individual messages all join together to provide side vision or peripheral vision as well as sharp central reading vision. Glaucoma can permanently damage the optic nerve, causing blind spots in areas of vision to develop. If glaucoma is undiagnosed, the optic nerve sustains irreversible considerable damage and may even be destroyed, resulting in blindness.

Glaucoma is detectable by measuring the intraocular pressure of the eye. Increased elevations of intraocular pressure are indicative of glaucoma situations or possible glaucoma situations. As shown in FIG. 1, clear transparent liquid flows through the inner eye continuously to maintain the structure of the eye, in particular, the cornea. If the outflow or drainage system within the eye becomes blocked, as shown in FIG. 2 for any reason, the fluid backs up within the inner eye causing the fluid pressure to increase and thus causing damage to the optic nerve. The possibility of damage to the optic nerve increases with increasing pressure. The only preventative measure which can be taken is early detection of glaucoma by periodic testing of the intraocular pressure since an elevated intraocular pressure is clearly basic to the whole concept of glaucoma.

A variety of mechanisms have been devised to facilitate the measurement of the intraocular pressure. The common available instrument, known as a tonometer, has the following general operational characteristics. The tonometer measures the force necessary to applanate or flatten a given area of the cornea. The measurement is directly related to the intraocular pressure because the cornea is flattened only when the external force equals the force applied by the ocular pressure plus the force necessary to deform the corneal tissue. The transition of the shape of the cornea from convex to planar can be detected by a simple optical principle. When a reflecting surface is illuminated with a narrow beam of light, the intensity of the reflected light gathered by a converging lens is maximal when the reflective surface is flat. Thus, if the cornea is illuminated by a narrow beam of light, the output of a photodetector placed at the focal plane of the lens will be maximal when the cornea flattens. Further, the flattened area should ideally be located at the apex of the cornea and perpendicular to the optical axis of the eye. This precaution is taken to minimize the deformation of the eyeball and to reduce the subsequent artificial increase of intraocular pressure due to the measurement. It should be noted however that requirement of proper alignment is not always achieveable and some current tonometers have been designed to compensate for variations in the positioning of the measurement probe with respect to the optical axis of the eye. Finally, the last requirement for most currently available tonometers is that the application of the instrument on the eye be rapid and automatic.

There are an assorted variety of tonometers currently available for measuring the intraocular pressures of the eye. The basic apparatus is the "Goldmann" applanation-type tonometer which is either hand held or designed for use as a fixed-type instrument. With the applanation-type tonometer, an applanating surface is placed in contact with the cornea and a force applied and varied until a fixed diameter of applanation of the cornea is achieved. The force of application is measured once the fixed diameter of applanation is achieved and this force is used to determine the intraocular pressure of the eye. The applanation-type tonometer must be used with a topical anesthetic. Another type of tonometer is the schiotz-type or plunger-type tonometer. This tonometer is placed before the eye along the optical axis and a plunger is released which flattens the cornea to a specified diameter and measures the forces applied. Again, the schiotz tonometer requires the use of a topical anesthetic. The schiotz and applanation tonometers, while accurate in their measurement of intraocular pressure, are quite undesirable to the patient in that they require the use of a topical anesthetic and further require that the eye be contacted by a mechanical device. Any contact with the corneal tissue carries the risk of infection and corneal abrasion. It has also been found that the patient usually has a somewhat high level of fear and physical discomfort as a result of such eye contact. Thus, the patient will tend to avoid the procedure, if possible.

In an effort to limit contact with the eye and thereby lessen patient fear, new non-contact tonometers utilizing an air puff pressure generation on the eye have been developed. This system uses an air pulse generated from the ambient atmosphere with a reliable positive linear force time ramp. The air pulse impinges upon the cornea causing a gradual curvature reduction, applanation, and a finally slight concavity before the decaying force time ramp permits restoration. Telecentric optical electronic monitoring of the corneal vertex reflection uniquely identifies, in time, the applanation event. This system has been described in detail in the American Journal of Optometry and Archives of the American Academy of Optometry, Vol. 49, August 1972, No. 8 "A new tonometer system", Grolman. While the air puff type tonometer has eliminated the need for the use of any form of topical anesthetic, the air puff tonometer creates audible sounds and sends a strong surge of air to the eye. Such sounds and air surges are still causing physical or psychological discomfort in some patients. Therefore, there is still a need for an apparatus which provides an accurate measurement of the intraocular pressure without need for topical anesthetic, and without any discomfort to the patient whether psychological or physical.

SUMMARY OF THE INVENTION

The present invention provides a solution to the above-stated objective. The present invention provides an high frequency tonometer which operates to accurately measure intraocular pressure without applanation of the eye and without physical contact with the eye. Because there is no physical contact, there is no need for topical anesthetics. The present invention provides no abrupt or detached noise audible to the human ear. Finally, the high frequency tonometer achieves its measurement of intraocular pressure without need for detached light or air surges to the eye.

The tonometer of the present invention is highly sensitive in measuring the intraocular pressure and can give continuous data, if necessary, instead of one instantaneous measurement. This is important because intraocular pressure changes over time and may be affected by factors such as the heartbeat. Finally, the ultrasonic tonometer of the present invention provides no physical or psychological discomfort to the patient thereby helping to eliminate any patient resistance to the need for regular intraocular pressure measurements.

The tonometer of the present invention can be best understood with reference to the drawings and the following description of the preferred embodiment of the invention.

DETAILED DESCRIPTION OF THE PREFERRED EMBODIMENT

Figures 1, 2:
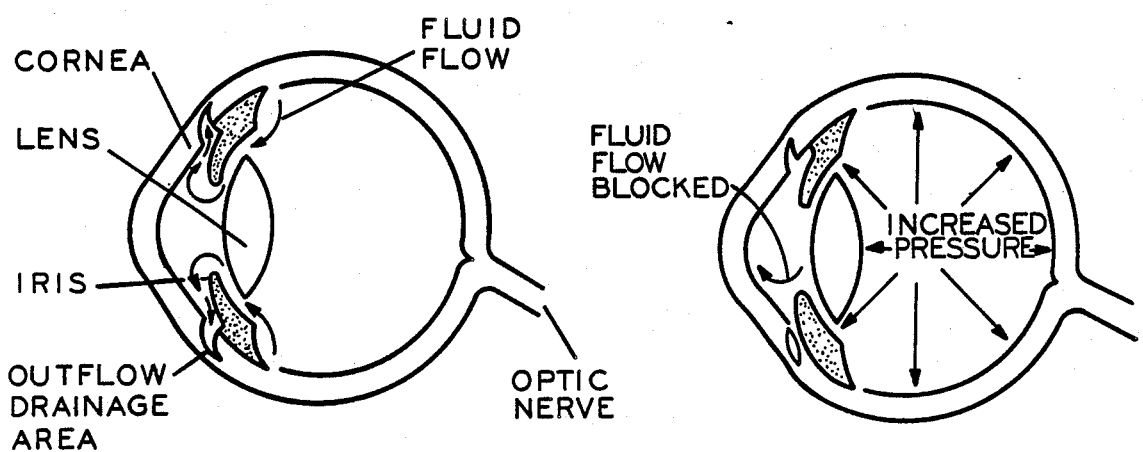
FIG. 1 is a schematic of a normal eye showing the fluid flow around the cornea of the eye.
FIG. 2 is a schematic showing a glaucomatous eye having increased intraocular pressure created by a build up of fluid within the eye.
Figure 3:
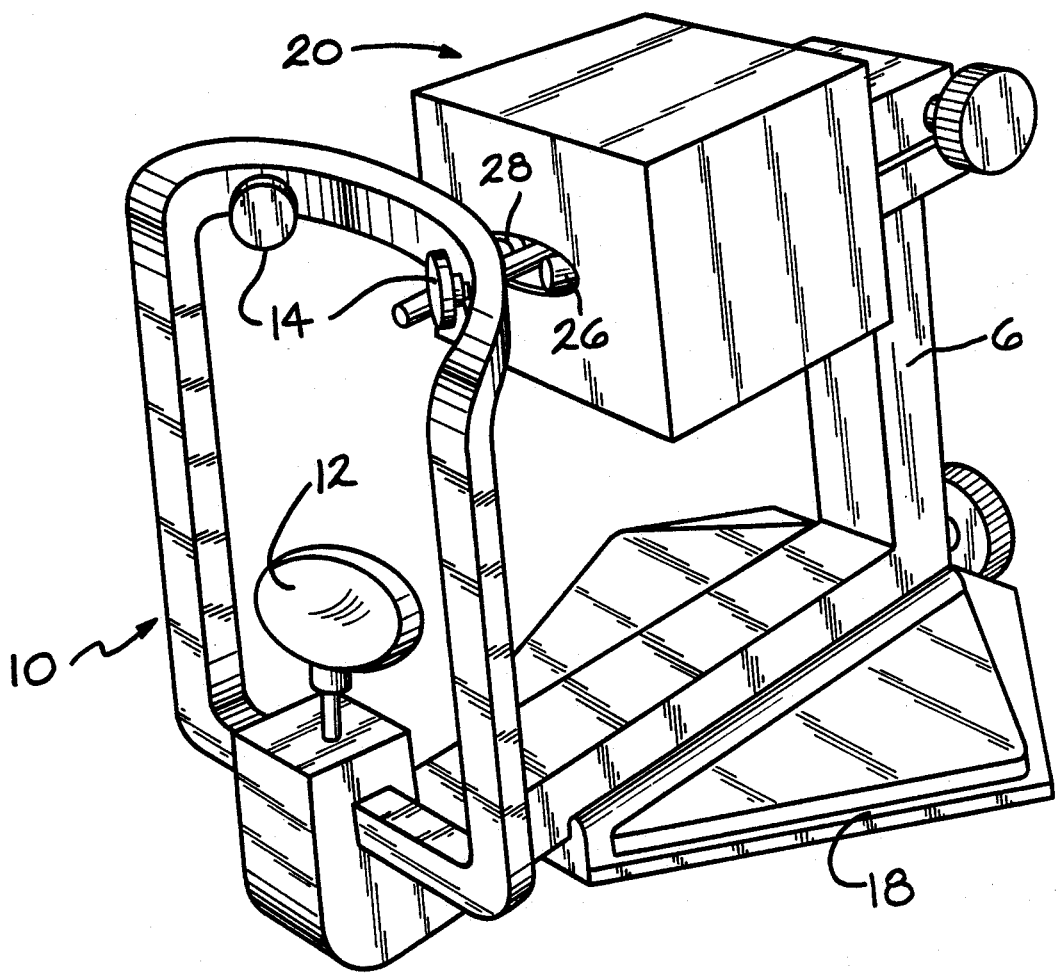
FIG. 3 is a perspective view in elevation of the high frequency tonometer of the present invention.

Referring to FIG. 3, the high frequency tonometer of the present invention includes a head rest 10 having a basic chin support 12 and forehead support 14. The head rest 10 is used to place the eyes of the patient in a motionless position. Fixed on a frame 6 in axial orientation with the eye is the tonometer 20 of the present invention. The tonometer 20 is mounted on a base 18 having the capability for movement about three axes. This adjustability enables the proper alignment of the tonometer 20 with the patient's eyes.

Figure 4:
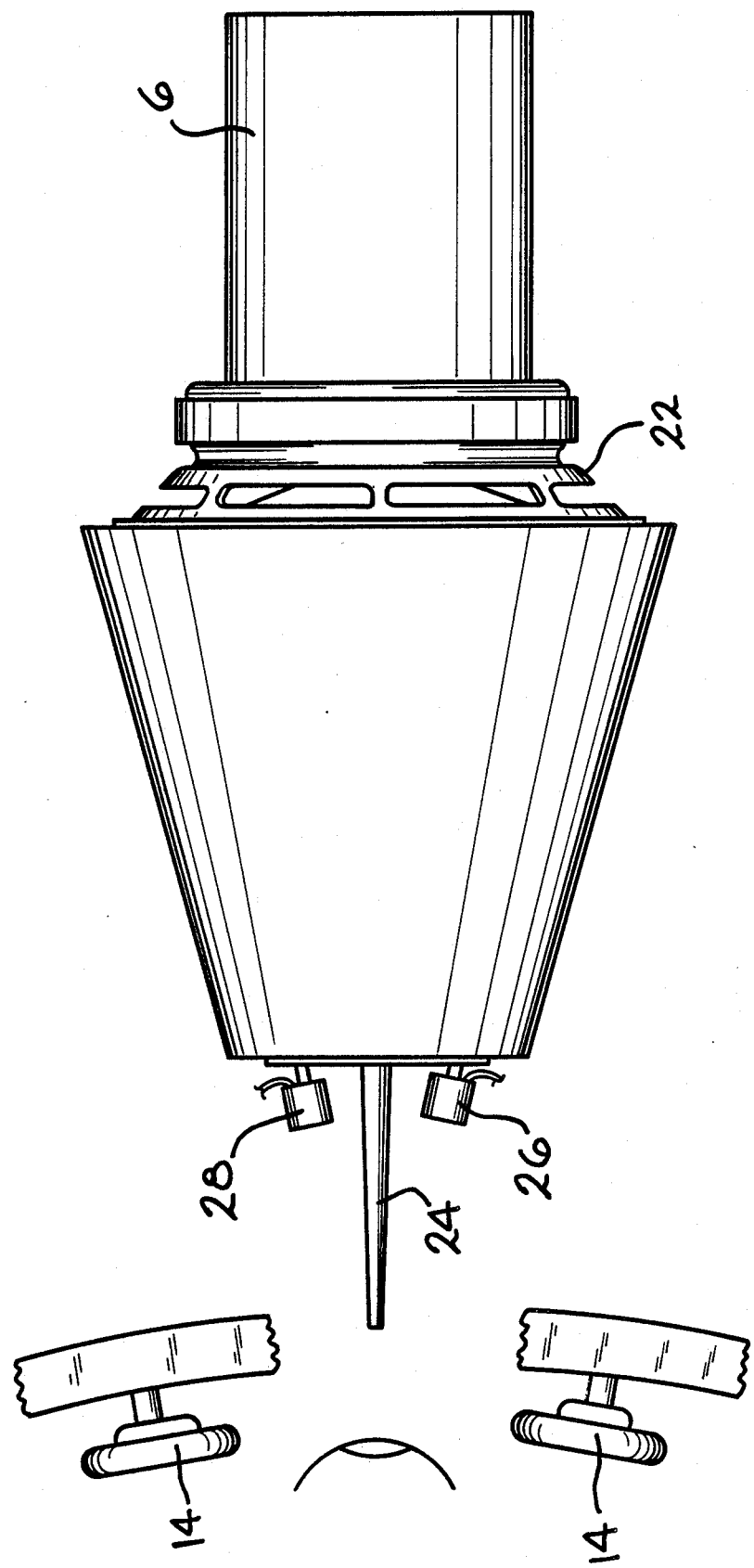
FIG. 4 is a perspective view in elevation of the high frequency tonometer of FIG. 3 with the outer casing removed.
Figure 5:
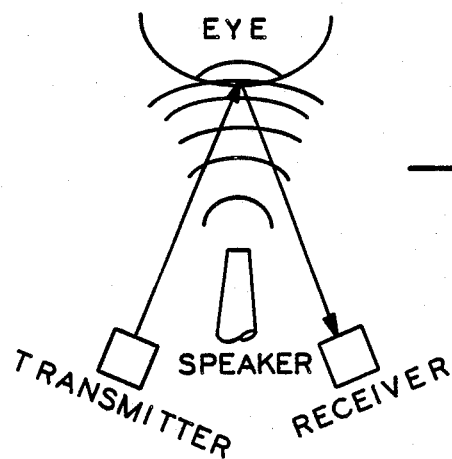
FIG. 5 is a diagrammatic representation of the basic operation of the high frequency tonometer of the present invention.

With reference to FIG. 4, the tonometer 20 of the present invention includes a speaker member 22 which produces a low frequency perturbing sound on the order of between 10–500 Hz. While there is no absolute requirement for the frequency, the low frequency is chosen so that it is toward the low end of the usual audible range of the average person preferably avoiding the line frequency of 60 Hz or its second harmonic of 120 Hz. The low frequency sound created by the speaker member 22 is formed as it travels through a perturbation cone member 24 and is directed toward a specified area of the corneal surface of the eye. The low frequency sound will cause a vibration of the corneal surface of the eye, the amplitude of which is dependent upon the intraocular pressure.

A transmitter 26 located immediately adjacent the perturbation cone member 24 is designed to transmit an high frequency wave towards the eye which is reflected to the receiver 28. While the figures show the transmitter 26 and receiver 28 angularly positioned with respect to the eye, they may also be oriented in a coaxial fashion. The high frequency waves being used are generally from 10 KHz to 1 MHz, just above the usual audible range for most people. While there is no restriction on the frequency to be used for the high frequency wave 40 KHz has been found to be effective. The high frequency wave must contact the cornea anywhere within the perturbed portion. The transmitter 26 and receiver 28 may also include cones (not shown) for shaping or directing the high frequency wave to and from the surface of the eye.

Figure 6:
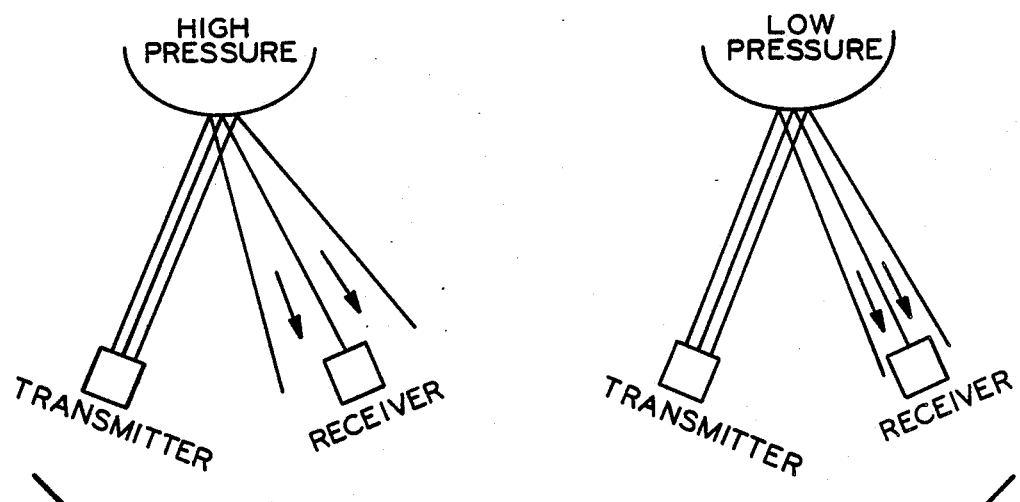
FIG. 6 is a diagrammatic representation of the basic principle of amplitude modulated detection as used by the present invention.
Figure 7:
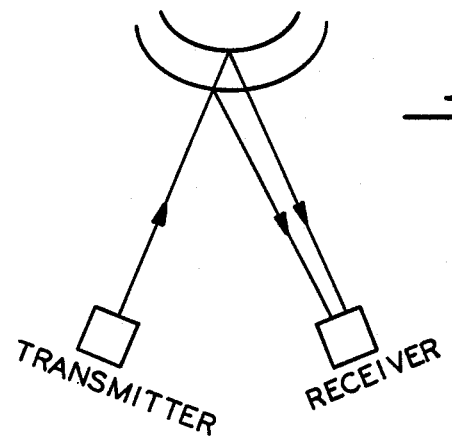
FIG. 7 is a diagrammatic representation of the basic principle of frequency modulated detection as alternatively used by the present invention.

The principle behind amplitude modulated detection is shown in FIG. 6. The curvature of the cornea depends upon the intraocular pressure. When the pressure is increased the cornea bulges and the incident high frequency beam is more diverged as it is reflected towards the receiver 28. Thus, for a fixed incident beam, the receiver will collect less of the refected beam during a phase of high intraocular pressure. As the surface of the eye is perturbed by the low frequency perturbing sound wave, the amplitude of the reflected high frequency wave is also modulated. By amplifying and detecting the modulation of the high frequency wave through the circuit of FIG. 8, an output signal is produced which is exactly dependent upon the intraocular pressure. An example of such an output signal in relation to the intraocular pressure is shown in FIG. 9.

Figure 8:
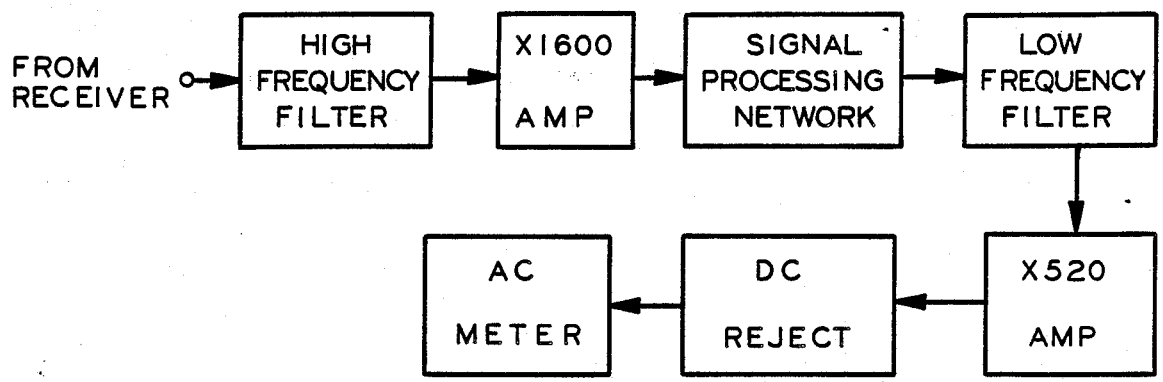
FIG. 8 is an electrical schematic of the output generator of the high frequency tonometer of the present invention.
Figure 9:
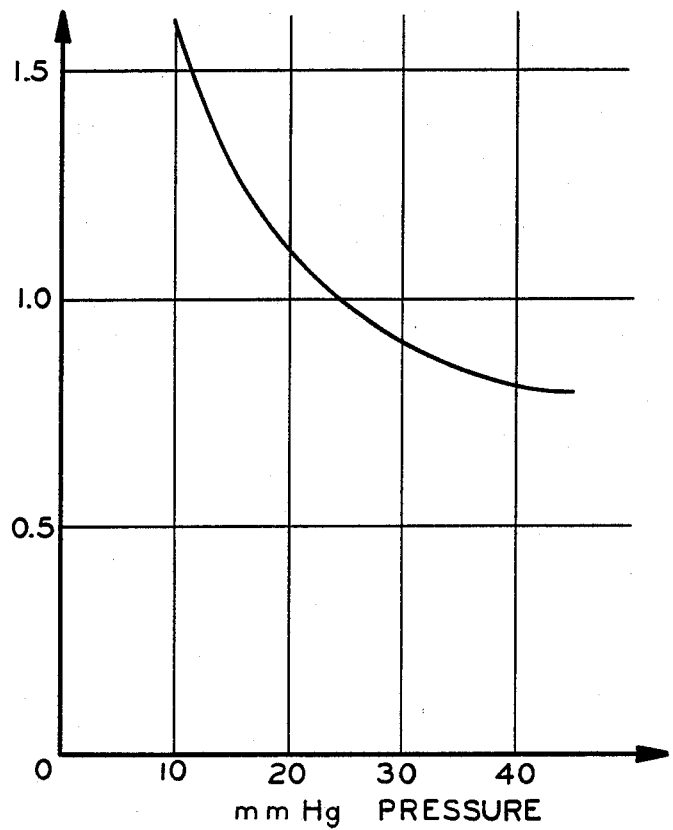
FIG. 9 is a graph showing a comparison of output voltage to intraocular pressure.

FIG. 8 shows a schematic diagram of the receiver circuit of the present invention. The signal from the receiver 28 (shown by the arrow) is a modulated high frequency wave; the result of the high frequency wave from the transmitter 26 reflecting off the perturbed portion of the cornea. The modulated high frequency wave includes the carrier frequency from the transmitter and side band frequencies from the perturbation of the low frequency signal. The high frequency filter passes the incoming carrier frequency from the transmitter but blocks or rejects any direct low frequency disturbance. The filtered signal is then amplified and sent to the signal processing network which demodulates the filtered signal to reproduce the desired low frequency signal caused by the speaker member 22. The demodulated signal is then passed through the low frequency filter to filter out the high frequency component which remains in the signal after detection. The filtered signal is then amplified and displayed for output. The output is directly proportional to the disturbance of the cornea caused by the low frequency perturbation beam.

The above description of the preferred embodiment is intended to illustrative in nature an is not intended to be limiting upon the scope of the following claims.

I claim:

1. A tonometer for use in the non-contact measurement of intraocular pressure of an eye comprising, in combination:

support means for placing such eye in a fixed position;

means for producing a low frequency perturbating sound wave positioned proximate of such eye wherein such perturbating sound wave is directed toward such eye for causing a vibration on the surface of such eye, the intensity of such vibration being dependent upon such intraocular pressure;

means for transmitting a high frequency wave positioned proximate said perturbating wave producing means, said high frequency wave being transmitted toward such eye for reflection of such perturbated surface of such eye;

means for receiving such reflected high frequency wave and detecting any modulation in the amplitude of such high frequency wave created by such vibration of the surface of such eye;

means for creating an output signal based upon such modulation; and, means for displaying such output signal for viewing.

2. The tonometer of claim 1, wherein said means for producing a perturbating sound includes a speaker capable of producing a sound wave having a frequency in the range of 10–500 Hz.

3. The tonometer of claim 1, wherein said transmitting means includes a transducer capable of producing a sound wave having a frequency in the range of 10 KHz–1 MHz.

4. A method for the measuring of the intraocular pressure of an eye comprising the steps of:

placing such eye in a fixed position;

directing a low frequency perturbating sound wave toward such eye for causing a vibration on the surface of such eye, the intensity of such vibration being dependent upon such intraocular pressure;

transmitting a high frequency wave toward such perturbated surface of such eye for reflection off of such surface of such eye;

detecting any modulation in the amplitude of such reflected high frequency wave;

developing an output signal based upon such modulation; and, displaying such output signal for viewing.

* * * * *